United States Patent
Wolter (10) Patent No.: US 9,439,695 B2
(45) Date of Patent: *Sep. 13, 2016

(54) OSTEOSYNTHESIS SYSTEM FOR THE MULTIDIRECTIONAL, ANGULAR-STABLE TREATMENT OF FRACTURES OF TUBULAR BONES COMPRISING AN INTRAMEDULLARY NAIL AND BONE SCREWS

(71) Applicant: Dietmar Wolter, Hoisdorf (DE)

(72) Inventor: Dietmar Wolter, Hoisdorf (DE)

( * ) Notice: Subject to any disclaimer, the term of this patent is extended or adjusted under 35 U.S.C. 154(b) by 147 days.

This patent is subject to a terminal disclaimer.

(21) Appl. No.: 14/229,242

(22) Filed: Mar. 28, 2014

(65) Prior Publication Data

US 2014/0296854 A1  Oct. 2, 2014

(30) Foreign Application Priority Data

Mar. 28, 2013  (DE) .......................... 10 2013 005 414

(51) Int. Cl.
| A61B 17/56 | (2006.01) |
| A61B 17/58 | (2006.01) |
| A61F 2/30 | (2006.01) |
| A61B 17/72 | (2006.01) |

(52) U.S. Cl.
CPC .......... *A61B 17/725* (2013.01); *A61B 17/7241* (2013.01); *A61B 17/7283* (2013.01)

(58) Field of Classification Search
CPC ..... A61B 17/68–17/688; A61B 17/72–17/748
USPC ...................................................... 606/62–68
See application file for complete search history.

(56) References Cited

U.S. PATENT DOCUMENTS

| 2,658,508 A | * | 11/1953 | Gibson | A61B 17/60 606/314 |
| 3,596,656 A | * | 8/1971 | Kaute | A61B 17/746 411/531 |
| 3,670,724 A | * | 6/1972 | Bosacco | A61B 17/1753 606/64 |
| 3,709,218 A | * | 1/1973 | Halloran | A61B 17/72 606/64 |
| 3,744,488 A | * | 7/1973 | Cox | A61B 17/72 606/309 |

(Continued)

FOREIGN PATENT DOCUMENTS

DE  19629011 A1  1/1998

*Primary Examiner* — Eduardo C Robert
*Assistant Examiner* — Michelle C Eckman
(74) *Attorney, Agent, or Firm* — Vidas, Arrett & Steinkraus, P.A.

(57) ABSTRACT

An osteosynthesis system for treating fractures of tubular bones includes an intramedullary nail with an elongated nail body consisting of a hard metal material with two end sections and a middle section that has at least one transverse screw hole close to the end for screwing in at least one bone screw into each end section. The nail body has a through-channel for pushing through a guide element, in the middle section on the side of the through-channel with the lowest wall thickness, at least two transverse one-sided screw holes for screwing in bone screws are placed proximate to a fracture, all one-sided screw holes are formed as inlays made out of soft metal material securely joined to the nail body, and bone screws with an initial thread consisting of hard metal material that can be screwed into the bone and screw holes while forming threads.

16 Claims, 4 Drawing Sheets

(56) References Cited

U.S. PATENT DOCUMENTS

| | | | | |
|---|---|---|---|---|
| 4,622,959 A * | 11/1986 | Marcus | A61B 17/1721 | 606/64 |
| 4,653,487 A * | 3/1987 | Maale | A61B 17/7098 | 606/62 |
| 4,697,585 A * | 10/1987 | Williams | A61B 17/72 | 606/64 |
| 4,756,307 A * | 7/1988 | Crowninshield | A61B 17/7283 | 606/67 |
| 4,776,330 A * | 10/1988 | Chapman | A61B 17/72 | 606/64 |
| 4,919,666 A * | 4/1990 | Buchhorn | A61M 31/002 | 606/62 |
| 4,928,679 A * | 5/1990 | Chagneau | A61B 17/7283 | 606/62 |
| 5,034,013 A * | 7/1991 | Kyle | A61B 17/72 | 606/62 |
| 5,041,115 A * | 8/1991 | Frigg | A61B 17/72 | 606/62 |
| 5,066,296 A * | 11/1991 | Chapman | A61B 17/72 | 606/62 |
| 5,312,406 A * | 5/1994 | Brumfield | A61B 17/1721 | 606/64 |
| 5,350,379 A * | 9/1994 | Spievack | A61B 17/7216 | 606/63 |
| 5,374,235 A * | 12/1994 | Ahrens | A61B 17/7233 | 606/101 |
| 5,429,640 A * | 7/1995 | Shuler | A61B 17/7283 | 606/62 |
| 5,472,444 A * | 12/1995 | Huebner | A61B 17/7283 | 606/62 |
| 5,480,402 A * | 1/1996 | Kim | A61B 17/1725 | 606/64 |
| 5,573,536 A * | 11/1996 | Grosse | A61B 17/72 | 606/60 |
| 5,713,902 A * | 2/1998 | Friedl | A61B 17/1721 | 606/62 |
| 5,766,174 A * | 6/1998 | Perry | A61B 17/1725 | 606/62 |
| 5,814,047 A * | 9/1998 | Emilio | A61B 17/7266 | 606/302 |
| 5,971,986 A * | 10/1999 | Santori | A61B 17/7266 | 606/323 |
| 6,010,505 A * | 1/2000 | Asche | A61B 17/683 | 606/62 |
| 6,019,761 A * | 2/2000 | Gustilo | A61B 17/72 | 606/62 |
| 6,228,086 B1 * | 5/2001 | Wahl | A61B 17/7225 | 606/62 |
| 6,296,645 B1 * | 10/2001 | Hover | A61B 17/72 | 606/62 |
| 6,409,768 B1 * | 6/2002 | Tepic | A61B 17/1725 | 606/64 |
| 6,517,541 B1 * | 2/2003 | Sesic | A61B 17/72 | 606/62 |
| 6,524,314 B1 * | 2/2003 | Dean | A61B 17/72 | 606/64 |
| 6,547,791 B1 * | 4/2003 | Buhren | A61B 17/7208 | 606/62 |
| 6,692,496 B1 * | 2/2004 | Wardlaw | A61B 17/1725 | 606/64 |
| 8,092,454 B2 * | 1/2012 | Sohngen | A61B 17/744 | 606/62 |
| 8,454,605 B2 * | 6/2013 | Gradl | A61B 17/72 | 606/62 |
| 8,496,657 B2 * | 7/2013 | Bonutti | A61B 17/0401 | 606/62 |
| 8,562,606 B2 * | 10/2013 | Richter | A61B 17/1682 | 606/62 |
| 8,628,532 B2 * | 1/2014 | Ritchey | A61B 17/1725 | 606/62 |
| 8,632,543 B2 * | 1/2014 | Metzinger | A61B 17/7283 | 606/62 |
| 2002/0007185 A1 * | 1/2002 | Aghion | A61B 17/685 | 606/66 |
| 2002/0099379 A1 * | 7/2002 | Adam | A61B 17/72 | 606/67 |
| 2002/0103488 A1 * | 8/2002 | Lower | A61B 17/72 | 606/62 |
| 2002/0151898 A1 * | 10/2002 | Sohngen | A61B 17/68 | 606/62 |
| 2002/0173792 A1 * | 11/2002 | Severns | A61B 17/72 | 606/62 |
| 2003/0060890 A1 * | 3/2003 | Tarabishy | A61B 17/1617 | 623/22.12 |
| 2003/0069581 A1 * | 4/2003 | Stinson | A61B 17/921 | 606/62 |
| 2004/0158252 A1 * | 8/2004 | Prager | A61B 17/72 | 606/64 |
| 2004/0172026 A1 * | 9/2004 | Ekholm | A61B 17/72 | 606/62 |
| 2005/0065528 A1 * | 3/2005 | Orbay | A61B 17/1725 | 606/62 |
| 2005/0096656 A1 * | 5/2005 | Behrens | A61B 17/1721 | 606/64 |
| 2005/0124995 A1 * | 6/2005 | Reiley | A61B 17/15 | 606/62 |
| 2005/0187550 A1 * | 8/2005 | Grusin | A61B 17/72 | 606/62 |
| 2005/0245933 A1 * | 11/2005 | Sevrain | A61B 17/68 | 606/286 |
| 2005/0277936 A1 * | 12/2005 | Siravo | A61B 17/72 | 606/62 |
| 2006/0015101 A1 * | 1/2006 | Warburton | A61B 17/1668 | 606/62 |
| 2006/0084997 A1 * | 4/2006 | Dejardin | A61B 17/1725 | 606/62 |
| 2006/0095040 A1 * | 5/2006 | Schlienger | A61B 17/686 | 606/64 |
| 2006/0100624 A1 * | 5/2006 | Orbay | A61B 17/8061 | 606/62 |
| 2006/0111717 A1 * | 5/2006 | Saueressig | A61B 17/72 | 606/64 |
| 2006/0149248 A1 * | 7/2006 | Schlienger | A61B 17/72 | 606/64 |
| 2006/0161155 A1 * | 7/2006 | Schlienger | A61B 17/72 | 606/62 |
| 2006/0195099 A1 * | 8/2006 | Bottlang | A61B 17/8605 | 606/67 |
| 2006/0200142 A1 * | 9/2006 | Sohngen | A61B 17/72 | 606/62 |
| 2007/0005146 A1 * | 1/2007 | Heyligers | A61F 2/367 | 623/23.46 |
| 2007/0016203 A1 * | 1/2007 | Schlienger | A61B 17/72 | 606/64 |
| 2007/0055254 A1 * | 3/2007 | Ihde | A61C 8/0018 | 606/71 |
| 2007/0123876 A1 * | 5/2007 | Czartoski | A61B 17/72 | 606/62 |
| 2007/0123878 A1 * | 5/2007 | Shaver | A61B 17/72 | 606/64 |
| 2007/0156144 A1 * | 7/2007 | Ulrich | A61B 17/7283 | 606/62 |
| 2007/0219636 A1 * | 9/2007 | Thakkar | A61B 17/1721 | 623/18.11 |
| 2007/0270833 A1 * | 11/2007 | Bonutti | A61B 17/0401 | 606/28 |
| 2007/0270845 A1 * | 11/2007 | Watanabe | A61B 17/164 | 606/62 |
| 2007/0276385 A1 * | 11/2007 | Schlienger | A61B 17/72 | 606/71 |
| 2007/0299447 A1 * | 12/2007 | Watanabe | A61B 17/164 | 606/71 |
| 2008/0009869 A1 * | 1/2008 | Schlienger | A61B 17/72 | 606/64 |
| 2008/0009873 A1 * | 1/2008 | Yacoubian | A61B 17/72 | 606/305 |
| 2008/0021474 A1 * | 1/2008 | Bonutti | A61B 17/0401 | 606/64 |
| 2008/0221574 A1 * | 9/2008 | Cavallazzi | A61B 17/1739 | 606/62 |
| 2008/0221577 A1 * | 9/2008 | Elghazaly | A61B 17/744 | 606/64 |

(56) References Cited

U.S. PATENT DOCUMENTS

| | | | |
|---|---|---|---|
| 2008/0255558 A1* | 10/2008 | Schlienger | A61B 17/72 606/62 |
| 2008/0262496 A1* | 10/2008 | Schlienger | A61B 17/72 606/62 |
| 2008/0287949 A1* | 11/2008 | Keith | A61B 17/7233 606/62 |
| 2008/0306479 A1* | 12/2008 | Bernstein | A61B 17/1725 606/329 |
| 2008/0312657 A1* | 12/2008 | Griggs | A61B 17/7216 606/63 |
| 2009/0157078 A1* | 6/2009 | Mikol | A61B 17/864 606/62 |
| 2010/0023057 A1* | 1/2010 | Aeschlimann | A61B 17/0401 606/246 |
| 2010/0114097 A1* | 5/2010 | Siravo | A61B 17/686 606/62 |
| 2010/0137865 A1* | 6/2010 | Frankle | A61B 17/1725 606/64 |
| 2010/0174284 A1* | 7/2010 | Schwammberger | A61B 17/7283 606/62 |
| 2010/0211120 A1* | 8/2010 | Bonutti | A61B 17/0401 606/86 R |
| 2010/0331843 A1* | 12/2010 | Grusin | A61B 17/7225 606/64 |
| 2011/0118740 A1* | 5/2011 | Rabiner | A61B 17/7225 606/63 |
| 2011/0172667 A1* | 7/2011 | Richards | A61B 17/72 606/62 |
| 2011/0178521 A1* | 7/2011 | Siravo | A61B 17/725 606/64 |
| 2011/0218531 A1* | 9/2011 | Orbay | A61B 17/72 606/62 |
| 2011/0218585 A1* | 9/2011 | Krinke | A61B 17/17 606/86 R |
| 2011/0288598 A1* | 11/2011 | Moed | A61B 17/8625 606/303 |
| 2011/0295254 A1* | 12/2011 | Brunnarius | A61B 17/7258 606/64 |
| 2012/0143192 A1* | 6/2012 | Watanabe | A61B 17/7225 606/64 |
| 2012/0209268 A1* | 8/2012 | Overes | A61B 17/1725 606/62 |
| 2012/0226326 A1* | 9/2012 | Overes | A61B 17/72 606/329 |
| 2012/0330313 A1* | 12/2012 | Grady | A61B 17/7225 606/64 |
| 2013/0030436 A1* | 1/2013 | LeCronier | A61B 17/725 606/64 |
| 2013/0053847 A1* | 2/2013 | Siravo | A61B 17/7241 606/62 |
| 2013/0079829 A1* | 3/2013 | Globerman | A61B 17/1728 606/286 |
| 2013/0158553 A1* | 6/2013 | Nardini | A61B 17/863 606/64 |
| 2013/0204250 A1* | 8/2013 | McDevitt | A61B 17/0401 606/64 |
| 2013/0261622 A1* | 10/2013 | Bonjour | A61B 17/7233 606/64 |
| 2013/0331947 A1* | 12/2013 | Surma | A61B 17/1739 623/21.12 |
| 2014/0017391 A1* | 1/2014 | Smith | A61B 17/72 427/2.1 |
| 2014/0094802 A1* | 4/2014 | Simon | A61B 17/7241 606/64 |
| 2014/0316409 A1* | 10/2014 | Watanabe | A61B 17/72 606/62 |
| 2014/0378973 A1* | 12/2014 | Mueckter | A61B 17/744 606/64 |
| 2015/0142125 A1* | 5/2015 | Watanabe | A61B 17/725 623/21.12 |
| 2015/0157369 A1* | 6/2015 | Ehmke | A61B 17/7241 606/64 |
| 2015/0157370 A1* | 6/2015 | Gross | A61B 17/72 604/506 |
| 2015/0265323 A1* | 9/2015 | Sems | A61B 17/7233 606/64 |

* cited by examiner

OSTEOSYNTHESIS SYSTEM FOR THE MULTIDIRECTIONAL, ANGULAR-STABLE TREATMENT OF FRACTURES OF TUBULAR BONES COMPRISING AN INTRAMEDULLARY NAIL AND BONE SCREWS

CROSS-REFERENCE TO RELATED APPLICATIONS

This Utility Patent Application claims priority to DE 10 2013 005 414.1, filed on Mar. 28, 2014.

STATEMENT REGARDING FEDERALLY SPONSORED RESEARCH

Not applicable.

BACKGROUND OF THE INVENTION

The invention relates to an intramedullary nail osteosynthesis system for the multidirectional, angular-stable treatment of fractures of tubular bones.

Intramedullary nailing is a surgical method for treating fractures of tubular bones, in particular the large tubular bones of the upper leg (femur), shin bone (tibia) and upper arm bone (humerus). The intramedullary nail has an elongated nail body consisting of metal that is inserted into the intramedullary space of the tubular bone to bridge the fracture in order to fix the bone fragments during the healing process. After the bone heals, the intramedullary nail can be removed. The rapid mobilization and load-bearing capacity of the patient after the treatment are advantageous.

The method was developed and promoted by G. Küntschner. The method was clinically tested by him during the period of the Second World War and was then accepted worldwide. There have been numerous publications about this method and its improvements. Furthermore, it is the subject of numerous patent applications.

Intramedullary nailing is not considered positively by everyone. Primary criticisms are impairment to intramedullary space circulation, resulting malpositioning and serious infections.

Küntschner first developed an intramedullary nail with a V-shaped cross-section, and he also used an intramedullary nail in the form of a slotted metal tube in order to improve the retention of the intramedullary nail in the tubular bone. The enlarged contact surface between this nail and the tubular bone lead to a transfer of load and force over a greater surface. In order to enhance this effect, the intramedullary space was drilled out. This resulted in additional damage to the bone circulation. In order to enlarge the surface contact between the metal tube and bone, transverse screws at the nail ends can be introduced through the bone. To this end, the intramedullary nails have circular or slotted holes in the ends through which the locking screws can be guided.

Intramedullary nails that have a central through-channel are widespread. A guide wire or guide pin is introduced into the intramedullary space to set the intramedullary nail. The intramedullary nail is hammered into the intramedullary space using the guide element. To do this, a hammering element with a wide head is screwed onto the top end of the intramedullary nail. The intramedullary nail is driven in with a hammer. The guide element ensures that the intramedullary nail enters the other part of the fracture after leaving one part of the fracture.

In order to reduce vascular damage from drilling, so-called unreamed intramedullary nails were used in previous decades. These are solid intramedullary nails that generally do not have any cavity. They consist of solid material and therefore also offer the option of locking.

Intramedullary nails are shaped anatomically. Furthermore, they are available in different thicknesses and lengths. They are preferably manufactured from stainless steel or titanium alloy.

The generic DE 43 41 677 C1, the entire contents of which is incorporated herein by reference, describes a locking nail for treating bone fractures with an elongated body consisting of solid material that is rounded on the front distal end and has a proximal hammering end. Transverse bores are arranged along the elongated body to each accommodate a bone screw. Each transverse bore has a least one funnel-shaped opening that expands outward on one side of each transverse bore. The funnel-shaped openings are for easily guiding a drill bit that is imprecisely placed on the bone and does not precisely mate with the transverse bores through the respective transverse bore. Greater flexibility in the fixation of a locking nail is ensured by a plurality of transverse bores at a distance from each other, for example in the treatment of a comminuted fracture. Due to its small cross-section, the locking nail reduces the hazard of impaired circulation. The known locking nail is weakened by the many transverse bores with the funnel-shaped openings. The weakening exists in particular in the middle of the intramedullary nail which is subjected to the greatest stress. The danger therefore exists of the intramedullary nail breaking under stress.

DE 196 29 011 A1, the entire contents of which is incorporated herein by reference, describes an intramedullary nail that has a through-hole for each locking screw with funnel-shaped expansions on either side and a threaded area in the middle. The transitions between the expansions and threaded area are rounded. The through-holes are formed in inlays which are welded at their cylindrical outer perimeter to the basic material of the intramedullary nail. The basic material and locking screws consist of titanium with a greater hardness, and the inlay consists of titanium with a lesser hardness. Consequently, the locking screws can be screwed in at different angles (multidirectionally) while forming a thread into a bore of the bone on both sides of the intramedullary nail as well as into the through holes. This enables multidirectional, angular-stable locking. The reduced intramedullary nail cross-section at the through holes expanded in the form of a funnel weakens the intramedullary nail. Based on this principle, intramedullary nails were produced that have such multidirectionally interlockable screws at the ends of the intramedullary nails. The reduced cross-sections are uncritical at the ends of the intramedullary nails because the intramedullary nail is only subject to comparatively low stress at that location.

EP 1 143 867 B1, the entire contents of which is incorporated herein by reference, describes an intramedullary nail that has at least one through-hole on both sides of the fracture. On both sides, the through hole has areas that expand spherically outward and has a thread-bearing area in the middle. The entire intramedullary nail can consist of comparatively hard titanium. Locking pins are inserted in the through holes on both sides of the fracture. A locking pin is conical and has threads on both ends for screwing into the bone that consist of a harder titanium material. In between, it has a conical jacket region that consists of a softer titanium material. When screwing in the locking pin through a bore in the bone into a through-hole, the locking pin forms a thread in the bone on both sides of the intramedullary nail, and the thread of the through-hole forms a thread in the jacket region of the locking pin. The locking pin can be screwed with the intramedullary nail with angular stability in different angular alignments. A disadvantage of this intramedullary nail is the weakening of the cross-section in the area of the through-holes that can cause failure under stress. In addition, it was revealed that forming a thread by screwing a soft pin part into a hard female thread is problematic.

Despite the described advantages, the healing process is lengthy, even with intramedullary nailing. During the healing process, the bone can only be subject to limited stress.

Against this background, an object of the invention is to provide an osteosynthesis system with an intramedullary nail and bone screws that more effectively supports the healing process and increases the load-bearing capacity of the tubular bone during the healing process.

BRIEF SUMMARY OF THE INVENTION

The osteosynthesis system according to the invention for treating fractures of tubular bones comprises an intramedullary nail with an elongated nail body consisting of a hard metal material with two end sections and a middle section therebetween. The nail body has at least one transverse screw hole close to the end for screwing in at least one bone screw in each end section. Furthermore, the nail body has a through-channel arranged off-center in the cross-section of the nail body for pushing through a guide wire, guide pin or another guide element. Furthermore in the middle section on the side of the through-channel with the lowest wall thickness, the nail body has at least two transverse one-sided screw holes at a distance from each other in the longitudinal direction of the elongated nail body for screwing in bone screws proximate to a fracture. All one-sided screw holes are formed in inlays (insert elements) consisting of a soft metal material that is securely joined to the elongated nail body. Furthermore, the osteosynthesis system comprises bone screws with an initial thread consisting of a hard metal material that can be screwed into the bone and screw holes while forming threads, whereby they securely join the bone and intramedullary nail.

The osteosynthesis system according to the invention is based on the awareness that the known locking of the intramedullary nail ends in the bone of the epiphysis which is soft due to its spongy structure does not significantly reduce the micro-movements of the ends of the fracture of the bone.

The reduction of micro-movements, especially under bending, shearing, and torsion is however essential for undisturbed healing.

The invention provides assistance in that it enables angular-stable interlocking of the intramedullary nail close to the fracture by screwing in bone screws into the cortical bone of the diaphysis and into the one-sided screw holes. The cortical diaphyseal bone has elevated mechanical strength due to its compact bone substance. Despite the weakening from the one-sided screw holes, the middle section of the intramedullary nail which is exposed to particularly high stress can be designed sufficiently stable.

This is because the one-sided screw holes only proceed from one longitudinal side of the nail body and do not extend to the opposite longitudinal side of the nail body, but rather only end at a distance from the opposite longitude side. The one-sided screw holes can be designed as blind holes. They preferably terminate within the through-channel of the nail body. Consequently, the cross-section of the nail body is weakened less by the one-sided screw holes than by screw holes that extend transversely through the entire cross-section as is the case with conventional intramedullary nails.

The through-channel (lumen) is arranged off-center in the cross-section of the nail body. The lumen of the nail body is thereby shifted from the center to one side toward a longitudinal side of the nail body such that the nail body has a thinner intramedullary nail wall on one side of the lumen than on the other side. The one-sided screw holes are arranged in the thinner intramedullary nail wall. By means of this arrangement, the cross-section of the nail body is weakened less than with a design in which the one-sided screw holes are arranged on one side of a through-channel arranged centrally in the cross-section of the nail body. The stability of the intramedullary nail is thereby further improved.

The strength of the bone and the intramedullary nail is impaired less by this unicortical anchoring of the intramedullary nail. This is sufficient to securely anchor the intramedullary nail in the bone because the material of the intramedullary nail (such as a solid pure titanium or a titanium alloy) has greater strength than the bone material. By screwing in a bone screw, a thread proceeding from a longitudinal side of the nail body can be formed in freely selectable angular alignments (multidirectional) in the inlay consisting of soft material (such as a soft pure titanium). Furthermore, in contrast to conventional intramedullary nails, the intramedullary nail according to the invention does not have any screw holes with funnel-shaped expansions for screwing in a bone screw in a multidirectional manner into an inlay in the interior of the intramedullary nail. Strong weakening of the intramedullary nail cross-section from screw holes expanded in a funnel-shaped manner can be avoided.

The deformation of the intramedullary nail while being pounded into the tubular bone can make it difficult to find the one-sided screw holes. There is therefore no guarantee that a drill bit for pre-drilling a hole in the bone by means of a setting device temporarily affixed to the end of the intramedullary nail can be precisely aligned with the one-sided screw holes. The bone holes can beat predrilled and the bone screws can be set with the assistance of an x-ray device for determining the position of the one-sided screw holes. Since the bone screws can be screwed multidirectionally into the intramedullary nail, it is easier to find the one-sided screw holes.

The intramedullary nail is preferably shaped anatomically. One end section is preferably angled slightly relative to the middle section of, for example, an intramedullary nail for the lower leg bone (tibia). The end section with which the intramedullary nail is driven forward into the bone is preferably tapered at its end.

The intramedullary nail can have different cross-sectional shapes. For example, it can have a circular cross section and a triangular cross-section (possibly with radii at the three "corners"), or a clover-leaf-shaped cross-section. Furthermore, the intramedullary nail can have grooves and/or ribs distributed on the outside over the perimeter.

The nail body can be a solid nail body with a reamed through-channel. Alternately, the nail body is produced by reshaping a metal sheet into a tube with a circular, oval, cornered or different cross-section. Preferably, a sheet metal strip is shaped by being bent, folded or wound (overfolding) into a tube.

According to one embodiment, the intramedullary nail is slotted. The slot can extend over the entire length of the nail body, or only over the middle section. With a nail body made of a sheet metal strip, the slot is bordered by the longitudinal edges of the sheet metal strip. According to another embodiment, the nail body is closed at the longitudinal edges of the sheet metal strip by means of a weld seam.

According to one embodiment, the nail body is manufactured from a sheet metal strip that has a bulge extending in the longitudinal direction. The wall thickness of the sheet metal strip therefore varies in the transverse direction. Consequently, the tube produced from the sheet metal strip has a greater wall thickness on one side of the through-channel than on the opposite side. In addition, the wall thickness can vary in the longitudinal direction of the sheet metal strip such that the finished nail body has a greater wall thickness in the middle section under particular stress than in the two end sections. The wall thickness preferably varies gradually. However, the invention also includes embodiments where the wall thickness changes suddenly, for example such that the nail body has a consistently greater wall thickness in one cross-section in one half, and a consistently smaller wall thickness in another half.

The transverse, one-sided screw holes proximate to the end are all aligned at an angle relative to the longitudinal axis of the intramedullary nail at the respective location of the screw hole. They are preferably aligned at a right angle relative to the longitudinal axis. They can, however, also be aligned at a sharp angle relative to the longitudinal axis. Furthermore, different screw holes can be aligned relative to the longitudinal axis at different angles.

The multidirectional, angular-stable fixation of bone screws in bone plates, intramedullary nails and other connectors are described in DE 43 43 117 C2 and in EP 1 143 867 B1. According to advantageous embodiments of the invention, the fixations of the middle bone screws in the middle screw holes are designed as described in the two documents, the contents of which are hereby incorporated in the present patent application.

The nail body and initial threads of the bone screws each consist of a hard metal material, and the inlays consist of a soft metal material.

This means that the metal material of the inlays is softer than the metal material of the nail body and the metal material of the initial thread of the bone screws. Furthermore, the nail body in the initial thread of the bone screws can consist of metal materials of equal hardness, or metal materials of different hardness.

The initial thread of the bone screws is the thread profile, or respectively the beginning of the thread profile, of the bone screws that forms a thread in the screw holes of the intramedullary nail. For example, only one outer layer comprising the thread profile, or a beginning of the thread profile, of the bone screw, or only the part of the threaded bolt having the initial thread, consists of the hard metal material, and the remainder of the bone screws consists of a soft metal material. The bone screws preferably consist completely of the hard metal material.

The nail body and initial thread of the bone screws preferably consist of a titanium alloy, or a hard pure titanium, or another hard titanium material. The titanium alloy preferably comprises titanium, vanadium and aluminium. In addition, it preferably comprises approximately 95% titanium and a total of approximately 5% vanadium and aluminium. More preferably, a grade 5 or higher titanium alloy, or grade 4 or 3 pure titanium is used for the nail body and/or the bone screws.

The inlays preferably consist of a soft pure titanium. More preferably, grade 0, 1, or 2 pure titanium is used for the inlays. The inlays can consist of a different material than pure titanium that possesses a hardness less than the material of the nail body and than the material of the middle bone screws, e.g., a titanium niobium alloy.

Instead of a titanium material, other materials can be used for the nail body and/or the bone screws that possess a greater hardness than the material of the inlays. The nail body and bone screws can consist of the same or different materials.

According to one embodiment, the inlays are inserted into transverse one-sided holes in the nail body. The one-sided holes extend from one longitudinal side of the nail body into the nail body and terminate therein at a distance from the opposite longitudinal side. The one-sided holes can be designed as blind holes. They preferably terminate within the through-channel of the nail body. According to another embodiment, the one-sided holes terminate in the through-channel, and the inlays do not extend into the through-channel, or only block a part of its cross-section.

The inlay preferably entirely fills the one-sided hole in the nail body so that the one-sided hole weakens the cross-section of the intramedullary nail as little as possible. Gaps in which bacteria can collect can also be thereby avoided. According to one preferred embodiment, the inlay has a press fit in the one-sided hole. According to another embodiment, the outer perimeter of the inlay is connected to the inner perimeter of the hole, and/or the peripheral outer edge of at least one front face is connected to a peripheral edge of the one-sided hole. The connection between inlay and nail body is preferably a welded connection. The connection is preferably created by diffusion welding or laser beam welding. Alternatively, the inlays can be fastened in the holes in the intramedullary nail by being screwed in and/or riveted.

According to one embodiment of the intramedullary nail with a through hole, there are, in one or more cross-sections that are offset in the longitudinal direction of the nail body, differently aligned one-sided screw holes into which the bone screws can be screwed from different directions.

According to another embodiment, the nail body has a reinforced cross-section, at least in the area of the one-sided screw holes. According to another embodiment, the reinforcement of the cross-section is a sheet metal strip that is fixed on the longitudinal side of the nail body opposite the one-sided screw hole, for example by means of welding. The sheet metal strip preferably consists of the same metal material as the nail body.

According to another embodiment, an outer side surface of the inlay is flush with the longitudinal-side outer surface (lateral surface) of the nail body, and/or an inner side surface of the inlay is flush with a longitudinal-side inner surface of the nail body bordering the through-channel. This prevents the inlay from projecting from and adding bulk to the outer surface, and/or prevents the inlay from hindering the insertion of the guide element. To achieve the flush section of the inlay with the nail body, finish work can occur after connecting the inlay to the nail body.

According to another embodiment, the screw holes close to the end in at least one end section are through holes that extend transversely through the nail body.

It is not problematic to design the screw holes close to the end as through holes since the stress on the nail body in the area of the end sections is less than in the middle section.

Furthermore, the locking of the bone screws on both sides of the end section is promoted because the tubular bone is more voluminous at the joint so that there is sufficient bone material available to accommodate bone screws that project on both sides of the intramedullary nail. In addition, the transmission of force over as large a surface as possible is advantageous in the area of the epiphysis and metaphysis because it prevents excessive stress on the bone material.

According to another embodiment, the screw holes close to the end are formed in inlays that are arranged in through-holes of the nail body close to the end which extend transversely through the entire cross-section. The filling of the holes close to the end with inlays, and the connection of the inlay to the nail body preferably occurs in the above-described manner. If the holes close to the end intersect a through-channel, two insert bodies are fixed in the hole on different sides of the through-channel according to one embodiment. According to another embodiment, the screw holes close to the end are also one-sided screw holes.

If more than two one-sided screw holes are distributed over the middle section in the longitudinal direction, the surgeon, depending on the application, can insert bone screws just in the two suitable one-sided screw holes that are closest to the fracture. The other one-sided screw holes can remain unused. The intramedullary nail can therefore be used for fractures supported in completely different ways. The complexity of the support is reduced. According to one preferred embodiment, two to six inlays with one-sided screw holes are distributed in the longitudinal direction over the middle section.

According to another embodiment, a plurality of screw holes close to the end in at least one end section are arranged distributed in the longitudinal direction and/or the peripheral direction of the nail body. Depending on the application, the surgeon can select suitable screw holes close to the end to insert bone screws. In at least one end section, there are preferably two to three screw holes close to the end. It is also preferable for the angular distance between the neighboring screw holes close to the end to be approximately 90°.

According to one embodiment, fill bodies with a thread consisting of a hard metal material and/or bone screws are screwed into at least the one-sided screw holes while forming threads. The fill bodies (dummies) consist of a metal material that is harder than the inlays, at least in the area of the thread profile. They preferably consist entirely of the hard metal material. They preferably have the same hardness as the initial thread on the bone screws. The fill bodies at least partially compensate for the weakness of the implant from the screw holes.

All one-sided screw holes are preferably filled with dummies before surgery. If the surgeon chooses the method of interlocking the intramedullary nail close to the fracture, before inserting the intramedullary nail he can remove the fill bodies from the screw holes that appear useful for multidirectional angular-stable locking close to the fracture. The surgeon can base the decision on an x-ray of the fracture.

Once the bone screws are screwed into the screw holes close to the fracture, they at least partially compensate for the weakening of the implant by the screw holes close to the fracture. If the surgeon chooses to exclusively fill screw holes close to the end with locking screws, he leaves the fill bodies in the one-sided screw holes in order to increase the strength of the intramedullary nail. This embodiment is particularly advantageous with an intramedullary nail that has a plurality of one-sided screw holes in the middle section. Before inserting the intramedullary nail, the surgeon removes only the fill bodies from the one-sided screw holes that are closest to the fracture. The other fill bodies remain in the one-sided screw holes. Preferably at the end of surgery, all of the nail holes are either filled with a thread-creating screw or a dummy.

The osteosynthesis system with intramedullary nails that has a plurality of one-sided screw holes with fill bodies in the middle section is useful for a number of different applications. Only different sizes and different designs for different tubular bones need to be stocked. This reduces the complexity of stocking.

The osteosynthesis system can also be used for treating fractures close to the joint, in particular for fractures in the area of the metaphysis. In these applications, interlocking close to the fracture is feasible by screwing at least one bone screw into a screw hole close to the end that is close to the fracture, and at least one bone screw into a one-sided screw hole close to the fracture.

According to a preferred embodiment, the fill body does not project out of the hole to the inside and/or outside. This prevents the fill body from adding bulk and/or prevents the hindrance of the insertion of a guide element if it is not removed before inserting the intramedullary nail.

According to another embodiment, the bottom side and/or top side of the fill body is adapted to the contour of the inner side surfaces and/or the outer side surface of the nail body.

According to another embodiment, the bone screws and/or the fill bodies have a conical threaded pin. The ability of the middle bone screws to be screwed in multiple directions into the one-sided screw holes is promoted by the conical shape of the threaded pin. The length of the fill bodies preferably corresponds to the length of the one-sided screw hole. This prevents the threaded pin from adding bulk. The length of the threaded pin of the bone screws preferably corresponds to the length of the one-sided crew hole plus the wall thickness of the cortical bone of the tubular bone for which the osteosynthesis system is intended, and the distance between the intramedullary nail and cortical bone.

The osteosynthesis system preferably comprises bone screws for one-sided screw holes with different lengths and/or bone screws for screw holes close to the end with different lengths. The surgeon fills the screw holes with bone screws of suitable length.

According to another embodiment, the bone screws have a disc-shaped screw head. The disk-shaped screw head adds only a little bulk to the outside of the bone. The disc-shaped screw head preferably has a smooth underside in order to prevent damage to the bone surface.

According to another embodiment, the bone screws and/or fill bodies have a tool drive on the outer end. The tool drive is for example a slot, external polyhedron, internal polyhedron, Phillips drive, pozidriv, Torx drive, spline drive, Tri-Wing, Torq-set, pentalobular drive.

According to another embodiment, the inlays have a projecting peripheral projection on the inner perimeter of the screw hole, or a peripheral sequence of projections in which a thread can be formed by screwing in a bone screw or a fill body. The projection forms a shapeable level that facilitates the formation of a thread and prevents chip formation. Embodiments of a multidirectional, angular-stable locking with a shapeable projection are described in EP 1 143 867 B1, the entire contents of which is incorporated herein by reference. In this regard, reference is made to EP 1 143 867 B1, the entire contents of which is incorporated herein by reference, the content of which is hereby incorporated into this application.

The nail body has a through-channel for pushing through a guide element. This "reamed intramedullary nail" can be advantageously inserted with a guide element. The guide element is removed after inserting the intramedullary nail. Then the bone screws are introduced, the tips of which can partially extend into the cavity in the intramedullary nail.

According to another embodiment, the osteosynthesis system comprises a guide wire, guide pin or another guide element. According to another embodiment, the guide element has a cross-section corresponding to the cross-section of the through-channel, or a part of the cross-section of the through-channel not blocked by the inlays and/or the fill bodies, so that the guide element can be shoved through the through-channel. With a guide element with a partial cross-section, the locking screws and/or the fill bodies can engage in the through-channel. The partial cross-section is selected so that the guide element can be shifted in the through-channel past the bone screws and/or the fill bodies.

BRIEF DESCRIPTION OF THE SEVERAL VIEWS OF THE DRAWINGS

The invention will be further explained below with reference to the accompanying drawings of exemplary embodiments. The drawings show.

DETAILED DESCRIPTION OF THE INVENTION

While this invention may be embodied in many different forms, there are described in detail herein a specific preferred embodiment of the invention. This description is an exemplification of the principles of the invention and is not intended to limit the invention to the particular embodiment illustrated According to FIGS. 1 and 2, an intramedullary nail 1 comprises an elongated nail body 2 with a circular cross-section 3 and a through-channel 4 arranged off-center relative to the cross section 3. The lumen of the through-channel 4 is circular. In a proximal end section 5 and a distal end section 6 of the nail body 2, there are three transverse proximal screw holes 7 close to the end and three distal screw holes 8 close to the end. In a middle section 9 of the body 2, there are five one-sided screw holes 10.

The elongated nail body is manufactured from a titanium alloy or grade 3 or 4 pure titanium.

Figure 2:
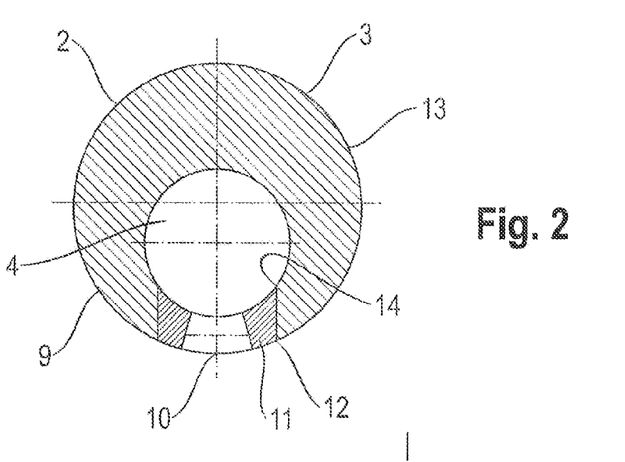
FIG. 2 The intramedullary nail in a cross-section of a one-sided screw hole.

The one-sided screw holes 10 are each formed in a hollow cylinder inlay 11.

The inlays 11 are manufactured from grade 0, 1 or 2 pure titanium.

Each inlay 11 is inserted snugly in a circular one-sided hole 12 in the longitudinal-side outer surface 13 of the nail body 2. The one-sided holes 12 extend up to the longitudinal-side inner surface 14 of the nail body 2 that border the through-channel 4. They are each formed in the thinner intramedullary nail wall.

The inlays 11 are welded to the nail body 2 and are flush on the outside with the longitudinal-side outer surface 13 of the nail body 2, and are flush on the inside with the longitudinal-side inner surface 14 of the nail body 2. The one-sided screw holes 10 are only arranged on one side of the through-channel 4. The thicker intramedullary nail wall in the middle section 9 of the nail body 2 does not have any one-sided screw holes 10 and is therefore not weakened.

Figure 1A:
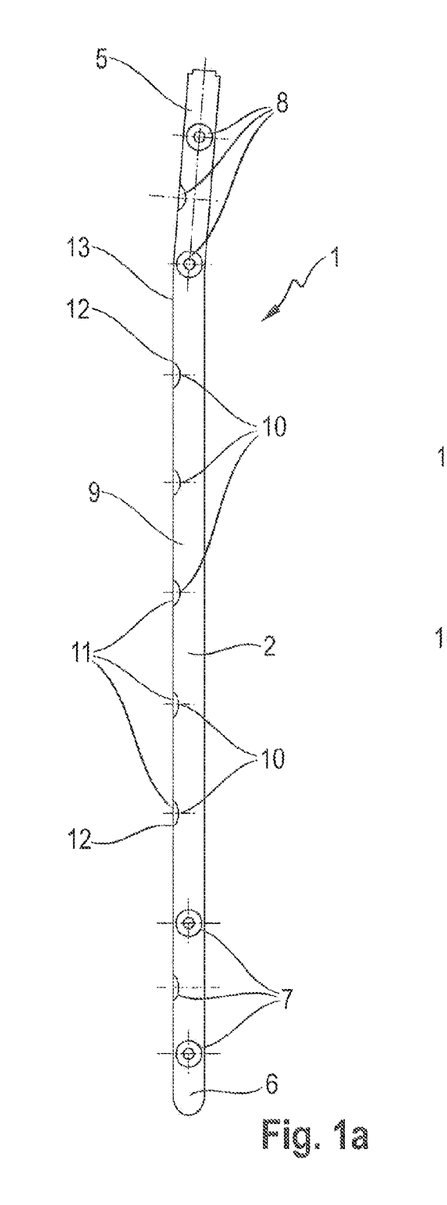
FIG. 1a A side view of an intramedullary nail.
Figure 1B:
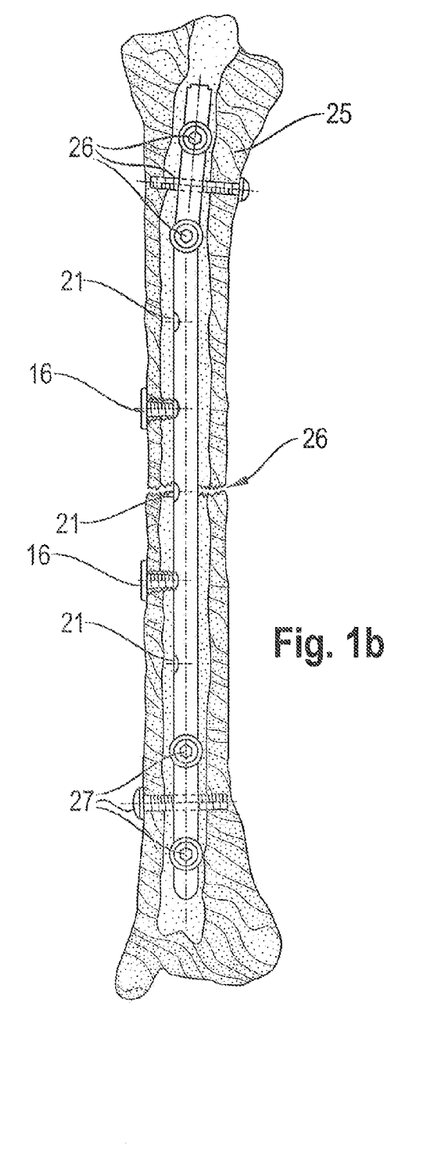
FIG. 1b The intramedullary nail with fill bodies, bone screws close to the end and close to the fracture in a tubular bone in a longitudinal section of the tubular bone.
Figure 1C:
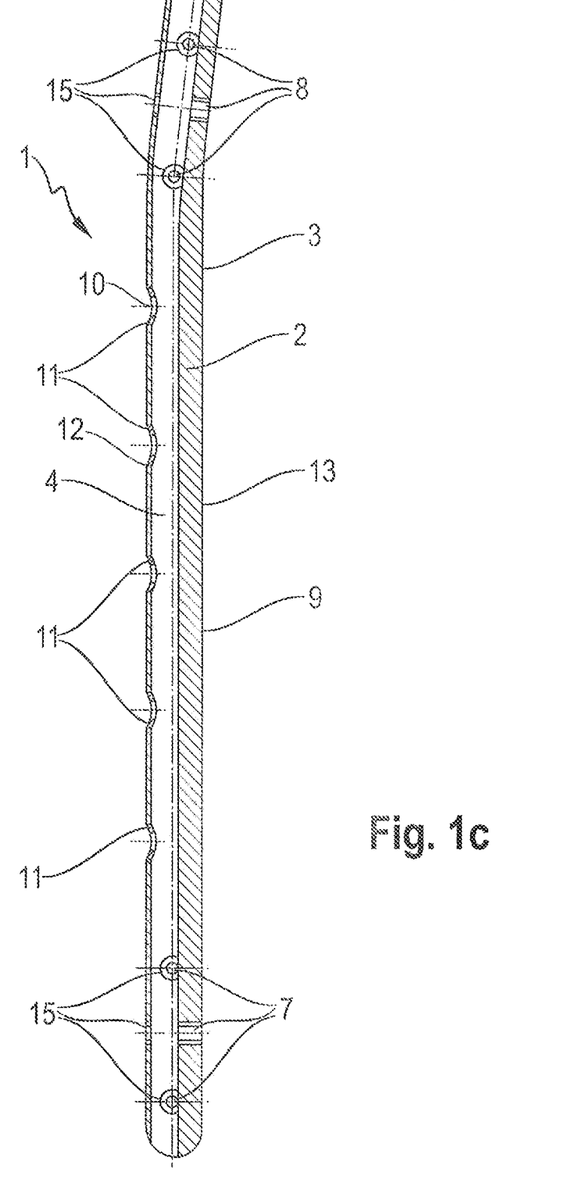
FIG. 1c A longitudinal section of the intramedullary nail.

The screw holes 7, 8 close to the end extend transversely through the cross-section of the nail body 2, i.e., they have openings in the longitudinal outer surface 13 on two opposing sides of the nail body 2. The screw holes 7, 8 close to the end each have a preformed inner thread 15 in the example. Alternately, each screw hole 7, 8 close to the end is formed in an inlay 11 that is arranged in a transverse hole close to the end with the nail body 2.

Figure 3:
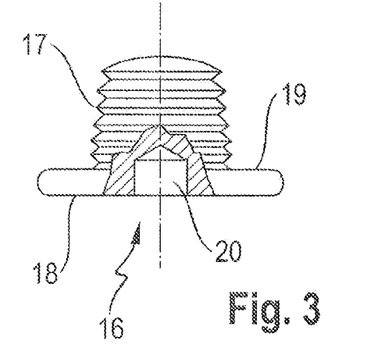
FIG. 3 A side view of a bone screw for a one-sided screw hole.
Figure 8:
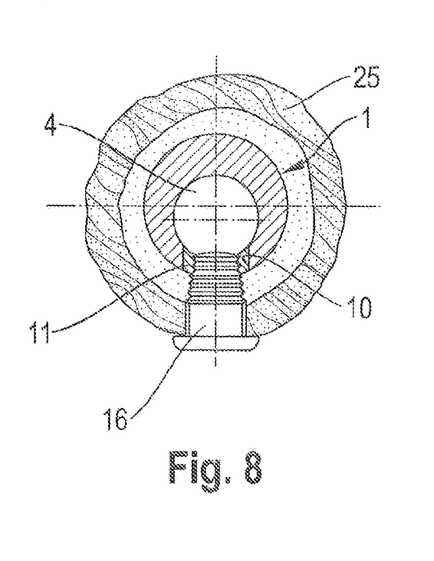
FIG. 8 The intramedullary nail in the tubular bone in a cross-section of a bone screw close to the fracture.

According to FIG. 3, a bone screw 16 for a one-sided screw hole 10 has a conical threaded pin 17 and a disc-shaped screw head 18. The maximum outer diameter of the threaded pin 17 approximately corresponds to its length. The bottom side 19 of the screw head 18 is smooth. The top side 20 of the screw head 18 has a tool drive. FIG. 8 shows a longer bone screw 16.1 with a threaded bolt 17 that is connected by means of a threadless pin section 17.1 to the screw head 18.

Figure 4:
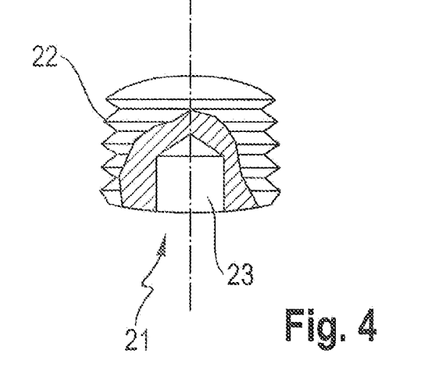
FIG. 4 A side view of a fill body.

According to FIG. 4, a fill body 21 only consists of a threaded pin 22. This is designed like the threaded pin 17 of the middle bone screw 16. The fill body 21 does not have a screw head. On the top side 23, the threaded pin 21 has a tool drive. Its top side 23 is rounded corresponding to the outer side surface of the nail body.

Before inserting the intramedullary nail 1, all of the one-sided screw holes 10 are filled with fill bodies 21 that are screwed into the inlays 11 while forming threads. The fill bodies 21 are preferably screwed into the inlays 11 perpendicular to the longitudinal axis of the nail body 2.

Before inserting the intramedullary nail 1, the surgeon removes the fill bodies 21 from the two one-sided screw holes 10 between which the fracture is arranged after inserting the intramedullary nail 1.

Figure 5:
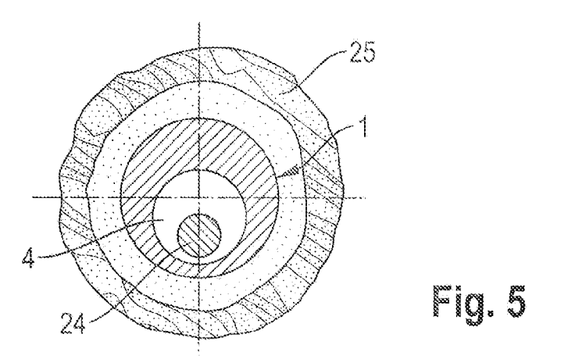
FIG. 5 A cross-section of the intramedullary nail with a guide wire in a tubular bone.
Figure 6:
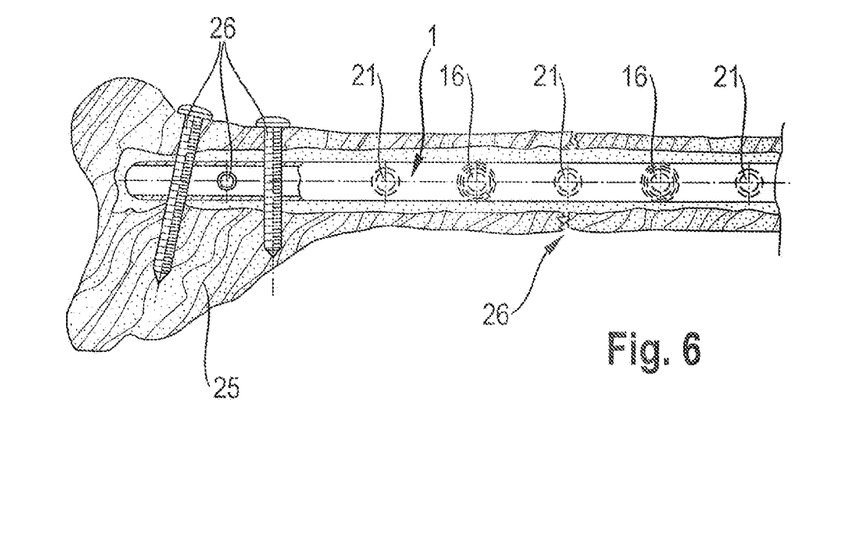
FIG. 6 Top part of the intramedullary nail in a partial longitudinal section in the tubular bone in another longitudinal section of the tubular bone.
Figure 7:
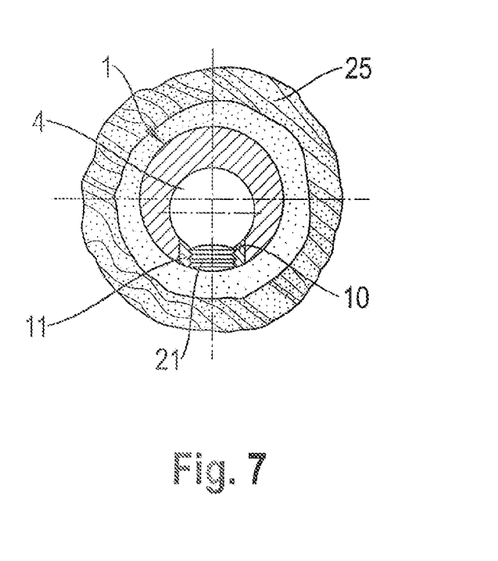
FIG. 7 The intramedullary nail in the tubular bone in a cross-section of a fill body.

According to FIG. 5, the intramedullary nail 1 can be inserted via a guide wire 24 into a tubular bone 25 with the fracture 26. The fill bodies 21 do not hinder this because they do not extend into the through-channel 4.

According to FIGS. 1b and 6 to 8, proximal and distal bone screws 25, 27 are screwed into the proximal and distal screw holes 7, 8 close to the end, and bone screws 16 are screwed in an angularly stable manner into the two middle screw holes 10 close to the fracture in a selectable angular alignment. In addition to the proximal and distal locking, this yields unicortical interlocking of the intramedullary nail 1 close to the fracture.

All middle screw holes 10 are either filled with fill bodies 21 or bone screws 16 so that the weakening of the cross-section of the nail body 4 is largely compensated by the screw holes 10.

The osteosynthesis system accelerates the healing of the fracture and improves the load bearing capacity of the bone during healing.

This completes the description of the preferred and alternate embodiments of the invention. Those skilled in the art may recognize other equivalents to the specific embodiment described herein which equivalents are intended to be encompassed by the claims attached hereto.

What is claimed is:

1. An osteosynthesis system for treating fractures of tubular bones comprising an intramedullary nail (1) with an elongated nail body (2) consisting of a hard metal material with two end sections (5, 6) and a middle section (9) therebetween that has at least one transverse screw hole (7) close to the end for screwing in at least one bone screw (25, 27) into each end section (6), wherein:
- the nail body (2) has a through-channel (4) arranged off-center in the cross-section of the nail body (2) for pushing through a guide element (24),
- in the middle section (9) on the side of the through-channel (4) with the lowest wall thickness, at least two transverse one-sided screw holes (10) at a distance from each other in the longitudinal direction of the nail body for screwing in bone screws (16) are placed proximate to a fracture, the at least two transverse screw holes (10) being one-sided and only formed in wall having the lowest thickness,
- all at least two transverse one-sided screw holes are formed as inlays (11) made out of soft metal material securely joined to the nail body (2), and
- bone screws (16) with an initial thread consisting of hard metal material that can be screwed into the bone and the at least two transverse one-sided screw holes (10) while forming threads, whereby they securely join the bone and intramedullary nail.

2. The osteosynthesis system according to claim 1, wherein the inlays are inserted into the at least two transverse one-sided holes in the nail body (2).

3. The osteosynthesis system according to claim 1, wherein the nail body (2) is a solid nail body and the through-channel is a reamed through-channel (4).

4. The osteosynthesis system according to claim 3, wherein the at least two transverse one-sided holes terminate (12) in the through-channel (4), and the inlays (11) do not extend into the through-channel (4), or only blocks a part of its cross-section.

5. The osteosynthesis system according to one of claim 3, with a guide wire or guide pin (24) with a cross-section corresponding to the cross-section of the through-channel (4), or a part of the cross-section of the through-channel (4) not blocked by the inlays and/or the fill bodies.

6. The osteosynthesis system according to claim 1, wherein the nail body (2) is manufactured by bending, folding or winding a sheet metal strip with a wall thickness that varies in the transverse direction.

7. The osteosynthesis system according to claim 1, wherein an outer side surface of the inlays (11) are flush with a longitudinal-side outer surface (13) of the nail body (2), and/or an inner side surface of the inlays (11) are flush with a longitudinal-side inner surface (14) of the nail body (2) bordering the through-channel (4).

8. The osteosynthesis system according to claim 1, wherein the inlays (11) hollow cylinders.

9. The osteosynthesis system according to claim 1, wherein the inlays of the at least two transverse one-sided screw holes comprise two to six inlays (11) distributed in the longitudinal direction over the middle section (9).

10. The osteosynthesis system according to claim 1, wherein fill bodies (21) with a thread consisting of a hard metal material and/or bone screws are screwed into the at least two transverse one-sided screw holes (10) while forming threads.

11. The osteosynthesis system according to claim 10, wherein the fill bodies (21) do not project out of the at least two transverse one-sided screw holes (10) to the outside and/or the inside, or only block a part of the cross-section of the through-channel (4).

12. The osteosynthesis system according to claim 10, wherein the fill bodies (21) have a groove at one end that terminates in a screwed position of the fill body (21) approximately flush with the inner side surface (14) of the nail body (2).

13. The osteosynthesis system according to claim 1, wherein the at least two transverse one-sided bone screws have a disk-shaped screw head (18), and/or the at least two transverse one-sided bone screws and/or the fill bodies (21) have a conical threaded pin (17, 22).

14. The osteosynthesis system according to claim 1, wherein the at least one transverse screw holes close to the end are through holes that extend transversely through the nail body (2).

15. The osteosynthesis system according to claim 1, wherein the at least on transverse close to the end in at least one of the two end sections are arranged distributed in the longitudinal direction and/or the peripheral direction of the nail body (2).

16. The osteosynthesis system according to claim 1, wherein the hard metal material of the nail body (2) and/or of the bone screws (25, 27) and/or of the fill bodies (21) is a titanium alloy or another hard titanium material, and/or wherein the soft metal material of the inlays is a pure titanium or another soft titanium material.

\* \* \* \* \*